United States Patent [19]

Hamburger

[11] 4,161,522

[45] Jul. 17, 1979

[54] METHOD FOR BLOCKING ALLERGIC RESPONSES

[75] Inventor: Robert N. Hamburger, La Jolla, Calif.

[73] Assignee: The Regents of the University of California, Berkeley, Calif.

[21] Appl. No.: 940,323

[22] Filed: Sep. 7, 1978

Related U.S. Application Data

[63] Continuation-in-part of Ser. No. 652,868, Jan. 27, 1976, which is a continuation-in-part of Ser. No. 565,425, Apr. 4, 1975, abandoned.

[51] Int. Cl.$^2$ .................. A61K 37/00; C07C 103/52
[52] U.S. Cl. ............................ 424/177; 260/112.5 R
[58] Field of Search ................ 424/177; 260/112.5 R

[56] References Cited

U.S. PATENT DOCUMENTS

| | | | |
|---|---|---|---|
| 3,466,368 | 9/1969 | Sela et al. | 424/177 |
| 3,597,409 | 8/1971 | Breuer et al. | 260/112 B |
| 3,664,994 | 5/1972 | Perper | 260/112 B |
| 3,763,135 | 10/1973 | Shanbrom | 260/112 B |
| 3,778,426 | 12/1973 | Hamburger | 260/112.5 R |
| 3,778,426 | 12/1973 | Naijar | 260/112.5 R |

FOREIGN PATENT DOCUMENTS

| | | |
|---|---|---|
| 957892 | 0000 | United Kingdom. |
| 1060400 | 0000 | United Kingdom. |
| 1212533 | 0000 | United Kingdom. |
| 1250361 | 0000 | United Kingdom. |
| 1259870 | 0000 | United Kingdom. |
| 1268463 | 0000 | United Kingdom. |
| 1287125 | 0000 | United Kingdom. |
| 1287601 | 0000 | United Kingdom. |
| 1311103 | 0000 | United Kingdom. |
| 1374329 | 0000 | United Kingdom. |

OTHER PUBLICATIONS

Terry et al., Chem. Abstr., 74, 11458j, 1971.
Ishizaka et al., Chem. Abstr., 80, 808666, 1974.
Tomioka, Chem. Abstr., 80, 25696w, 1974.
Bennich et al., Chem. Abstr., 76, 84322m, 1972.
Pettit, G. R., "Synthetic Peptides", 2, Van Nostrand Reinhold Co., N.Y., 1971, pp. 84–91.
Hamburg, R. A., Peptide Inhibition of the Prausnitz–Kustner Reaction, Science 189, 4200, pp. 389–393.
Stewart, J. M. and J. D. Young, "Solid Phase Peptide Syn." Freeman & Co., San Francisco 1969, pp. 1–18.
Bennich et al., Adv. in Immunol.; 13, 1–55 (1971).
Ishizaka et al., "Specific Receptors of Antibodies Antigen and Cells," 3rd Internat. Convec. on Imnunol.; 1972.
Fredholm et al., Acta Physiol. Scand., 1967, 69, 304–312.

*Primary Examiner*—Delbert R. Phillips
*Attorney, Agent, or Firm*—Phillips, Moore, Weissenberger, Lempio & Majestic

[57] ABSTRACT

A group of relatively low molecular weight polypeptides having from 3 to 10 amino acids block the allergic response. These "blocking" polypeptides have amino acid sequences corresponding to amino acid sequences appearing in the 2nd, 3rd and 4th domains of the epsilon chain of IgE. Certain derivatives of such polypeptides also exhibit "blocking" activity. Specific active "blocking" polypeptides are disclosed and the synthesis and use thereof are described.

17 Claims, No Drawings

METHOD FOR BLOCKING ALLERGIC RESPONSES

RELATED APPLICATIONS

This is a continuation-in-part of my application Ser. No.: 652,868, filed Jan. 27, 1976, which, in turn, is a continuation-in-part of application Ser. No.: 565,425, filed Apr. 4, 1975, now abandoned.

BACKGROUND OF THE INVENTION

The symptoms of human allergic disease or more properly the allergic syndrome, are brought about through the release into the organism of vasoactive amines, notably histamine. The histamine is normally stored in special cells known as mast cells and basophil leucocytes distributed throughout the organism. The mast cells are dispersed throughout human tissue structures, while the basophils circulate with the blood in the body, i.e., within the vascular system.

The above-noted cells manufacture and store histamine within their internal structures, and the histamine remains therein unless a specialized sequence of events occur to trigger the release of histamine from within the cell structures into the surrounding tissues and vascular system.

More specifically, histamine will be released in response to the presence of specific antigens (allergens) that gain entrance into the organism or may be released by the organism in response to some traumatic occurrence. However, the usual release of histamine from the mast cells or basophils is triggered by a necessary sequence of chemical and immunological events taking place on and in the mast cell and basophil structures.

Specifically, the allergen-mast cell (basophil) interaction is mediated by a group of proteins known as immnoglobulin E (IgE) that are manufactured within the body. The IgE manufactured by the human organism is a complex arrangement of polypeptide chains, each molecule of which may have certain variations in the sequence of amino acids in the polypeptide chain, but all of which in essence may be characterized as having a "Y" like structure, wherein the "tail" (actually the base of the "Y") (Fc) polypeptide portion or fragment contains a fixed sequence or "constant region" of peptides along the chain. The "heads" (which are equivalent to the upper arms of the "Y" structure) may have regions wherein the polypeptide chain varies (the variable region of the Fab) from molecule to molecule. Thus, the IgE molecules generally have identical "tail" peptide sequences but may have a great number of different "head" peptide sequences.

The allergic or immunologic release of histamine within the organism from the specialized mast cells and basophils can occur only under the following circumstances:

All mast cells or basophils possess a number of receptor sites that are available for "locking" onto the constant region or Fc portion of IgE molecules. These "binding sites" are specialized areas on the cell membranes wherein a special geometric or spatial molecular arrangement of molecules occurs, thus enabling this "binding or receptor site" to "lock" into the Fc fragment or a site in the constant region of the IgE molecule.

Should a wandering IgE molecule find a free "binding receptor site" on a mast cell or basophil, it locks or attaches at its Fc end onto the cell binding (receptor) site to secure the IgE molecule to the mast cell or basophil.

When the Fc portion of the IgE molecule is secured to the receptor "binding site", the upper arms of the "Y" shaped molecule (the F(ab) portion) are free to extend above the cell surface. These extended upper peptide chains in turn act as receptors to allergens which may be present in the organism's environment. If the polypeptide structure of the Fab portions are compatible with a particular allergen the allergen may attach to the outwardly extending Fab of the IgE polypeptide chain. Should such an attachment occur, the mast cell or basophil is automatically stimulated or "triggered" to release histamine from within its cell structure into the local environment of the mast cell or basophil. Once the histamine is released, the familiar "allergic symptoms" are manifested.

The present state of therapy of allergic disease includes hyposensitization (repeated injections of offending allergens to produce "blocking antibodies"), systemic therapy with anti-histamines (which compete with histamines released during the allergic reaction) and disodium cromoglycate (which may lower the amount of histamine released by allergic reactions). Corticosteroids, isoprenaline and theophylline as well as other medications are also utilized in the therapy of allergy. However, none of these afore-mentioned drugs or techniques interfere with the basic IgE-mast cell (basophil) reaction itself, and all have significant limitations in usefulness.

Another course of therapy suggested by the analysis above of the allergen-IgE-mast cell (basophil) reaction would be the introduction into the organism of a drug that would "block" the mast cell (basophil) receptor or binding sites against the attachment of the IgE molecule. Of equal importance would be a drug that would not only "block" the binding sites, but in additional would displace IgE from binding sites to which the IgE was already attached. Any filling up or diminution in the binding sites available for IgE attachment would quite obviously reduce the number of allergen-IgE-mast cell (basophil) reactions, and as a consequence, thereby reduce the release of histamine into the organism and thereby reduce or prevent the allergic reaction.

Some prior attempts have been made to use this therapeutic approach. For instance, in 1968 Stanworth, et. al. published in Lancet (July 6, 1968) a study wherein the whole Fc portion of the IgE as well as small proteolytic digestion fragments thereof were tested for their ability to suppress the allergic reaction. This study suggested that only the complete Fc fragment of IgE was as effective as the intact IgE Molecule in inhibiting allergic reaction while the digestion fragments were ineffective. That is, any fraction of the Fc peptide chain less than the entire Fc polypeptide was unable to prevent an induced allergic reaction. The Fc fragment itself cannot be used as a therapeutic agent or drug.

DESCRIPTION OF THE INVENTION

The present invention is directed to novel low molecular weight polypeptides which are useful as therapeutic agents in the treatment of allergic disease or the allergic syndrome.

More specifically, the present invention is directed to polypeptides containing from 3 to 10 amino acid residues, and certain dimers and lipophilic enhanced derivatives thereof, which have the property of blocking the human allergic response. These relatively short chain polypeptides correspond to sequences occuring in the second (C-2), third (C-3), and fourth (C-4) domains of the constant (Fc) region of the epsilon (ε) peptide chain of the IgE molecule.

The amino acid sequence of the entire ε chain has been recently determined by Bennich and his coworkers and reported in "Progress in Immunology II-Vol. 1: Immunochemical Aspects", July, 1974, pp. 49–58, North-Holland Publishing Company, Amsterdam, 1974. The sequence of the Fc region in which the amino acid sequences of the present invention occur is as follows, with the marginal numbers indicating the numerical position in the sequence of the amino acid to the right thereof:

265-(Met)-Asp-Val-Asp-Leu-Ser-Thr-Ala-Ser-Thr-Glu-Ser-Glu-Gly-Glu-Leu-Ala-Ser-Thr-Glu-Ser-Glu-Leu-Thr-289-Leu-Ser-Gln-Lys-His-Trp-Leu-Ser-Asp-Arg-Thr-Tyr-Thr-Cys-Glu-Val-Thr-Tyr-Glx-Gly-His-Thr-Phe-Glx-313-Asx-Ser-Thr-Lys-Lys-Cys-Ala-Asp-Ser-Asp-Pro-Arg-Gly-Val-Ser-Ala-Tyr-Leu-Ser-Arg-Pro-Ser-Pro-Phe-337-Asp-Leu-Phe-Ile-Arg-Lys-Ser-Pro-Thr-Ile-Thr-Cys-Leu-Val-Val-Asx-Leu-Ala-Pro-Ser-Lys-Gly-Thr-Val-361-Asn-Leu-Thr-Trp-Ser-Arg-Ala-Ser-Gly-Lys-Pro-Val-Asx-His-Ser-Thr-Arg-Lys-Glu-Glu-Lys-Gln-Arg-Asn-385-Gly-Thr-Leu-Thr-Val-Thr-Ser-Thr-Leu-Pro-Val-Gly-Thr-Arg-Asx-Trp-Ile-Glu-Gly-Glu-Thr-Tyr-Glx-Cys-409-Arg-Val-Thr-His-Pro-His-Leu-Pro-Arg-Ala-Leu-Met-Arg-Ser-Thr-Thr-Lys-Thr-Ser-Gly-Pro-Arg-Ala-Ala-433-Pro-Glu-Val-Tyr-Ala-Phe-Ala-Thr-Pro-Glu-Trp-Pro-Gly-Ser-Arg-Asp-Lys-Arg-Thr-Leu-Ala-Cys-Leu-Ile-457-Gln-Asn-Phe-Met-Pro-Glu-Asp-Ile-Ser-Val-Gln-Trp-Leu-His-Asn-Glu-Val-Gln-Leu-Pro-Asp-Ala-Arg-His-481-Ser-Thr-Thr-Gln-Pro-Arg-Lys-Thr-Lys-Gly-Ser-Gly-Phe-Phe-Val-Phe-Ser-Arg-Leu-Glu-Val-Thr-Arg-Ala-505-Glu-Trp-Gln-Glu-Lys-Asp-Glu-Phe-Ile-Cys-Arg-Ala-Val-His-Glu-Ala-Ala-Ser-Pro-Ser-Gln-Thr-Val-Gln-529-Arg-Ala-Val-Ser-Val-Asn-Pro-Gly-Lys

The novel compounds of the present invention are polypeptides comprising between 3 and 10 amino acids in sequence, said sequence selected from a portion of the above amino acid sequence; as well as the salts, esters, amides, N-acyl, O-acyl, certain dimers, and lipophilic enhanced derivatives thereof.

As set forth above and for convenience in describing this invention, the conventional abbreviations for the various amino acids are used. They are familiar to those skilled in the art; but for clarity, those with which this invention is concerned are listed below. All chiral amino acid residues referred to herein are of the natural or L-configuration unless otherwise specified. All peptide sequences mentioned herein are written according to the usual convention whereby the N-terminal amino acid is on the left and the C-terminal amino acid is on the right:

Asp = Aspartic Acid
Ala = Alanine
Arg = Arginine
Asn = Asparagine
Asx = Aspartic Acid or Asparagine (indicates uncertainty in degradation analysis)
Cys = Cysteine
Gly = Glycine
Glu = Glutamic Acid
Gln = Glutamine
Glx = Glutamic acid or Glutamine (indicates uncertainty in degradation analysis)
His = Histidine
Ile = Isoleucine
Leu = Leucine
Lys = Lysine
Met = Methionine
Phe = Phenylalanine
Pro = Proline
Ser = Serine
Thr = Threonine
Trp = Tryptophan
Tyr = Tyrosine
Val = Valine As used herein the term "salts" refers to both salts of a carboxyl group of the polypeptide chain as well as acid addition salts of an amino group of the polypeptide chain. Salts of a carboxyl group may be formed with either inorganic or organic bases. Inorganic salts include for example the alkali metal salts such as the sodium, potassium and lithium salts; the alkaline earth salts such as for example the calcium, barium, and magnesium salts; and the ammonium, ferrous, ferric, zinc, manganous, aluminum, manganic salts, and the like. Salts with organic amines include those formed, for example, with trimethylamine, triethylamine, tri(n-propyl)amine, dicyclohexylamine, β-(dimethylamino)ethanol, tris(hydroxymethyl)aminomethane, triethanolamine, β-(diethylamino)ethanol, arginine, lysine, histidien, N-ethylpiperidine, hydrabamine, choline, betaine, ethylenediamine, glucosamine, methylglucamine, theobromine, purines, piperazines, piperidines, caffeine, procaine, and the like.

Acid addition salts include, for example salts, with mineral acids such as for example hydrochloric acid, hydro-bromic acid, sulfuric acid, phosphoric acid, nitric acid and the like; and salts with organic acids such as for example acetic acid, oxalic acid, tartaric acid, succinic acid, maleic acid, fumaric acid, gluconic acid, citric acid, malic acid, ascorbic acid, benzoic acid, and the like.

As used herein, the term "esters" refers to esters of a carboxyl group of the polypeptide formed with straight or branched chain saturated aliphatic alcohols of from one to twelve carbon atoms, such as the methyl, ethyl, n-propyl, isopropyl, n-butyl, t-butyl, n-amyl, n-hexyl, octyl, decyl, and dodecyl esters.

As used herein the term "amides" refers to amides of a carboxy group of the polypeptide formed with ammonia, or with primary or secondary amines having up to 12 carbon atoms such as for example dimethylamine, diethyylamine, di(n-butyl)-amine, n-hexylamine, piperidine, pyrrolidine, morpholine, di(n-hexyl)amine, N-mthylpiperazine and the like.

"N-acyl derivatives" refer to those derivatives of an amino group of the polypeptide formed with acyl moieties (e.g. alkanoyl or carbocyclic aroyl groups) containing up to 12 carbon atoms, such as formamides, acetamides, benzamides, and the like. The N-acyl derivatives are of special interest, especially those which include strongly lipophilic properties, e.g., $C_8$ and higher, alkanoyl derivatives. As will be noted hereinafter, such lipophilic N-acyl derivatives appear to exhibit "blocking" activities on a par with the sample polypeptides.

"O-acyl derivatives" refer to those derivatives of a hydroxyl group of the polypeptide chain formed with acyl moieties (e.g. alkanoly or carbocyclic aroyl groups) containing up to 12 carbon atoms, such as formates, acetates, propionates, benzoates, and the like.

In some instances it is possible to cross-link the polypeptides to produce the dimer. Thus, for instance, where cysteine occurs in the amino acid sequence in the polypeptide, a cross-linking disulfide bridge may be formed with a corresponding cysteine (to form the equivalent amino acid cystine) to effectively cross-link two polypeptides. As will be noted hereinafter, blocking activity has been exhibited by such a polypeptide dimer.

In other instances, some activity has been exhibited by certain of the polypeptides disclosed wherein one or perhaps two of the amino acids in the normal $\epsilon$ chain sequence is replaced by another amino acid. Specific instances of such substituted polypeptides will be noted hereinafter.

Preferred polypeptides of this invention are those which have amino acid sequences that are non-analogous with comparable regions in other immunoglobulins. In this regard, the following peptides may be especially mentioned:

266-Asp-Val-Asp-Leu-Ser
271-Thr-Ala-Ser-Thr-Glu
266-Asp-Val-Asp-Leu-Ser-Thr-Ala-Ser-Thr-Glu
289-Leu-Ser-Gln-Lys-His
319-Ala-Asp-Ser-Asp-Pro-Arg
320-Asp-Ser-Asp-Pro-Arg
321-Ser-Asp-Pro-Arg
322-Asp-Pro-Arg
354-Ala-Pro-Ser-Lys-Gly-Thr
367-Ala-Ser-Gly-Lys-Pro
437-Ala-Phe-Ala-Thr-Pro-Glu-Trp-Pro-Gly-Ser
437-Ala-Phe-Ala-Thr-Pro
442-Glu-Trp-Pro-Gly-Ser
476-Pro-Asp-Ala-Arg-His-Ser
521-Ala-Ser-Pro-Ser-Gln as well as salts, esters, amides, N-acyl and O-acyl derivatives thereof.

A particularly preferred polypeptide is Asp-Ser-Asp-Pro-Arg.

The above list is not intended to be exhaustive and additional peptides having shorter sequences than the above, or having sequences with additional amino acids therein, or sequences taken from other regions of the C-2, C-3 or C-4 domains, are of importance.

In a second aspect, the present invention is directed to a method useful for preventing or relieving symptoms associated with allergic manifestations such as are brought about by antigen-antibody (allergic) reactions. The method hereof serves to block (i.e., inhibit or prevent) the effects of the allergic reaction when the subject polypeptide is administered in an effective amount. Thus this aspect of the present invention relates to a method useful for preventing or inhibiting the effects of allergic reaction which comprises administering to a mammalian subject (preferably a human) an effective amount of a polypeptide or derivative thereof as hereinabove described.

While the compounds of the present invention are believed to act by "blocking" IgE binding sites as described herein, it is not intended that the present invention be limited to any particular mechanism of action.

The present invention, in a third aspect, is directed to pharmaceutical compositions useful for blocking (i.e. preventing or inhibiting) the effects of the allergic reaction comprising an effective amount of a polypeptide or derivative thereof, as described hereinabove, in admixture with a pharmaceutically acceptable non-toxic carrier.

In the practice of the method of the present invention, an effective amount of a polypeptide or derivative thereof, or a pharmaceutical composition containing same, as defined above, is administered via any of the usual and acceptable methods known in the art, either singly or in combination with another compound or compounds of the present invention or other pharmaceutical agents such as antihistamines, corticosteroids, and the like. These compounds or compositions can thus be administered orally, sublingually, topically (e.g. on the skin or in the eyes), parenterally (e.g. intramuscularly, intravenously, subcutaneously or intradermally), or by inhalation, and in the form of either solid, liquid or gaseous dosage including tablets, suspensions, and aerosols, as discussed in more detail hereinafter. The administration can be conducted in single unit dosage form with continuous thereapy or in single dose therapy ad libitum.

In one preferred embodiment, the method of the present invention is practiced when the relief of symptoms is specifically required or perhaps imminent; in another preferred embodiment, the method hereof is effectively practiced as continuous or prophylactic treatment.

In view of the foregoing as well as in consideration of the degree or severity of the condition being treated, age of subject, and so forth, all of which factors being determinable by routine experimentation by one skilled in the art, the effective dosage in accordance herewith can vary over a wide range. Since individual subjects vary in their IgE content, an effective systemic dosage in accordance herewith can best be described as between $2 \times 10^3$ and $2 \times 10^6$ times the IgE content, on a molar scale. For an average subject this would be between about 0.5 and 500 mg/kg/day, depending upon the potency of the compound. Of course, for localized treatment, e.g., of the respiratory system, proportionately less material will be required.

Useful pharmaceutical carriers for the preparation of the compositions hereof, can be solids, liquids or gases; thus, the compositions can take the form of tablets, pills, capsules, powders, enterically coated or other protected formulations (such as by binding on ion exchange resins or other carriers, or packaging in lipid-protein vesicles or adding additional terminal amino acids or replacing a terminal amino acid in the L-form with one in the D-form), sustained release formulations, solutions (e.g. opthalmic drops), suspensions, elixirs, aerosols, and the like. The carrier can be selected from the various oils including those of petroleum, animal, vegetable or synthetic origin, for example, peanut oil, soybean oil, mineral oil, sesame oil, and the like. Water, saline, aqueous dextrose, and glycols are preferred liquid carriers, particularly (when isotonic) for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulation are described in "Remington's Pharmaceutical Sciences" by E. W. Martin. Such compositions will, in any event, contain an effective amount of the active compound together with a suitable amount of carrier so as to prepare the proper dosage form for proper administration to the host.

To be effective for the prevention or treatment of the allergic reaction it is important that the therapeutic agents be relatively non-toxic, non-antigenic and non-irritating at the levels in actual use. This has been demonstrated to be the case with all of the present compounds whose preparation is described hereinbelow.

The polypeptides of the present invention may be synthesized by any techniques that are known to those skilled in the peptide art. An excellent summary of the many techniques so available may be found in J. Meienhofer, "Hormonal Proteins and Peptides", Vol. 2, p. 46, Academic Press (New York), 1973 for solid phase peptide synthesis and E. Shroder and K. Lubke, "The Peptides", Vol. 1, Academic Press (New York), 1965 for classical solution synthesis.

In general, these methods comprise the sequential addition to a growing chain of one or more amino acids or suitably protected amino acids. Normally, either the amino or carboxyl group of the first amino acid is protected, by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

Protecting groups should have the properties of being stable to the conditions of peptide linkage formulation, while being readily removable without destruction of the growing peptide chain or racemization of any of the chiral centers contained therein.

Among the classes of amino protecting groups useful for stepwise synthesis of polypeptides are: (1) acyl type protecting groups illustrated by the following: formyl, trifluoroacetyl, phthalyl, toluenesulfonyl (tosyl), benzensulfonyl, o-nitrophenylsulfenyl, tritylsulfenyl, o-nitrophenoxyacetyl, chloroacetyl, acetyl, γ-chlorobutyryl, etc.; (2) aromatic urethan type protecting groups illustrated by benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl, 2-(pbiphenylyl) isopropyloxycarbonyl, 2-benzoyl-1-methylvinyl; (3) aliphatic urethan protecting groups illustrated by tert-butyloxycarbonyl, tert-amyloxycarbonyl diisopropylmethoxycarbonyl, isopropyloxycarbonyl, ethoxycarbonyl, allyloxycarbonyl; (4) cycloalkyl urethan type protecting groups illustrated by cyclopentyloxycarbonyl, adamantyloxycarbonyl, cyclohexyloxycarbonyl; (5) thio urethan type protecting groups such as phenylthiocarbonyl; (6) alkyl type protecting groups as illustrated by triphenylmethyl (trityl) and benzyl; and (7) trialkylsilyl groups such as trimethylsilyl.

Preferred protecting groups are tert-butyloxycarbonyl (t-BOC), and ter-amyloxycarbonyl (AOC).

Among the classes of carboxyl protecting groups useful for stepwise synthesis of polypeptides are: (1) substituted or unsubstituted aliphatic ester protecting groups such as methyl, ethyl, t-butyl, 2,2,2,-trichlorethyl and t-butyl esters; (2) aralkyl ester protecting groups such as benzyl, p-nitrobenzyl, p-methoxybenzyl, diphenylmethyl or triphenylmethyl (trityl) esters; (3) N-substituted hydrazides such as t-butyloxycarbonylhydrazides and carbobenzyloxycarbonylhydrazides; (4) amide protecting groups formed by condensation of a carboxyl moiety with e.g. ammonia, methylamine, ethylamine, diphenylmethylamine; and the like.

Hydroxyl groups of amino acids such as serine, threonine and hydroxyproline may be protected as aralkyl ethers such as benzyl ethers.

Suitable solid supports useful for the above synthesis are those materials which are inert to the reagents and reaction conditions of the stepwise condensation-deprotection reactions, as well as being insoluble in the media used. Materials that may be used include, for example, crosslinked polystyrene divinylbenzene resins, crosslinked polyamide resins, polyethyleneglycol resins, appropriately functionalized glass beads, and the like.

The first amino acid residue is linked to the solid support by forming a covalent bond with an active group on the resin. Suitable active groups for this purpose include, for example, chloromethyl, benzyhdrilamino, hydroxymethyl, phenacyl halide, dehydroalanine and the like. The preferred active group is chloromethyl. The first amino acid may be coupled to the preferred chloromethyl resin by one of several base catalyzed processes wherein the triethylamine, tetramethylammonium or cesium (or similar) salt of the carboxylic acid is heated with the resin in a solvent such as ethanol, dioxane, dimethylformamide, and the like.

Suitable reagents that effect amide formation between carboxyl and amino groups are known in the art and include, for example, (1) carbodiimides such as for example dicyclohexylcarbodiimide (DCC), (2) a carbodiimide plus an additive such as 1-hydroxybenzotriazole or ethyl 2-hydroximino-2-cyanoacetate; (3) alkyl chloroformates such as isobutylchloroformate or ethylchloroformate; (4) N-protected amino acids activated by formation of a suitable ester, for example, substituted phenyl esters, aryl or alkyl thio-esters, substituted 8-hydroxy isoquinoline esters, 2-thio-pyridyl esters and similar esters well known to those skilled in the art.

A preferred method for synthesizing the peptides of the present invention is the so-called "Merrifield" synthesis technique which is well known to those skilled in the art and is set forth in detail in the article entitled "Synthesis of a Tetrapeptide" by R. B. Merrifield, Journal of the American Chemical Society (Vol. 85, pp. 2149–2154 (1963) as well as Meienhofer, cited above.

In this preferred method a peptide of any desired length and of any desired sequence is produced through the stepwise addition of amino acids to a growing peptide chain which is bound by a covalent bond to a solid resin particle.

In the preferred application of this method the C-terminal end of the growing peptide chain is covalently bound to a resin particle and amino acids having protected amino groups are added in the stepwise manner indicated above. A preferred amino protecting group is the t-BOC group, which is stable to the condensation conditions and yet is readily removalbe without destruction of the peptide bonds or racemization of chiral centers in the peptide chain. At the end of the procedure the final peptide is cleaved from the resin, and any remaining protecting groups are removed, by treatment under acidic conditions such as, for example, with a mixture of hydrobromic acid and trifluoroacetic acid or with hydrofluoric acid, or the cleavage from the resin may be effected under basic conditions, for example, with triethylamine, the protecting groups then being removed under acid conditions.

The cleaved peptides are isolated and purified by means well known in the art such as, for example, lyophilization followed by either exclusion or partition chromatography on polysaccharide gel media such as Sephadex G-25, or countercurrent distribution. The composition of the final peptide may be confirmed by amino acid analysis after degradation of the peptide by standard means.

Salts of carboxyl groups of the peptide may be prepared in the usual manner by contacting the peptide with one or more equivalents of a desired base such as, for example, a metallic hydroxide base e.g., sodium hydroxide; a metal carbonate or bicarbonate base such as for example sodium carbonate or sodium bicarbonate; or an amine base such as for example triethylamine, triethanolamine, and the like.

Acid addition salts of the polypeptides may be prepared by contacting the polypeptide with one or more equivalents of the desired inorganic or organic acid, such as, for example, hydrochloric acid.

Esters of carboxyl groups of the polypeptides may be prepared by any of the usual means known in the art for converting a carboxylic acid or precursor to an ester. One preferred method for preparing esters of the present polypeptides, when using the Merrifield synthesis technique described above, is to cleave the completed polypeptide from the resin in the presence of the desired alcohol either under basic or acidic conditions, depending upon the resin. Thus the C-terminal end of the peptide when freed from the resin is directly esterified without isolation of the free acid.

Amides of the polypeptides of the present invention may also be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

N-acyl derivatives of an amino group of the present polypeptides may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O- acylation may be carried out together, if desired.

The coupling, deprotection/cleavage reactions and preparation of derivatives of the subject polypeptides are suitably carried out at temperatures between about $-10°$ and $+50°$ C., most preferably about $20°-25°$ C. The exact temperature for any particular reaction will of course be dependent upon the substrates, reagents, solvents and so forth, all being well within the skill of the practitioner. Illustrative reaction conditions for these processes may be gleaned from the examples.

The following examples are given to enable those skilled in the art to more fully understand and practice the present invention. They should not be construed as a limitation upon the scope of the invention, but merely as being illustrative and representative thereof.

EXAMPLE I

Preparation of the Tripeptide Asp-Pro-Arg 1.6 G. (5 mmoles) of t-Boc-nitroarginine are reacted with 10 g. of chloromethyl resin (beaded copolystyrene-2% divinyl benzene containing 0.5-1 meq. of chloromethyl groups per gram of resin) in a mixture of 1.4 ml. (10 mmoles) of triethylamine and 100 ml. of ethanol for 24 hours at 22° C. with constant stirring. The argininated resin is then washed thoroughly, successively, with acetic acid, absolute ethanol, water with increasing amounts of ethanol, then methanol and finally methylene chloride. The resin is then thoroughly dried in vacuo. Analysis revealed 0.05 mmole Arg/g. resin. 2.5 G. of the resin so prepared is placed in a Merrifield solid phase reaction vessel equipped for agitation and is put through the following DEPROTECTION CYCLE:

(a) with agitation, and at 22° C., the t-Boc group is cleaved with 10 ml. of 4 N HCl in dioxane for 30 minutes, (b) two washes with 10 ml. of dioxane, (c) two washes with 10 ml. of methylene chloride, (d) two washes with 10 ml. of chloroform, (e) the hydrochloride is neutralized with 10 ml. of triethylamine/chloroform (5:95), (f) two washes with 10 ml. of methylene chloride, (g) two washes with 10 ml. of chloroform.

The resin is then subjected to the SYNTHESIS CYCLE as follows: a ten-fold excess of t-Boc-proline (1.25 mmoles) in methylene chloride solution is added followed by 258 mg. (1.25 mmoles) of dicyclohexylcarbodiimide (DCC) and the mixture is shaken for 2 hours at 22° C. The resin is then washed three times each with 10 ml. portions of dioxane, chloroform, and methylene chloride; respectively.

The dipeptide resin is then subjected to the deprotection cycle and is reacted with a four-fold excess of t-Boc β-benzyl aspartate (0.5 mmoles) as described above in the synthesis cycle. An 0.5 g. portion of the resin is then removed from the reaction vessel and subjected to the CLEAVAGE PROCESS as follows:

The tripeptide resin (0.5 g.) is suspended in dry trifluoroacetic acid (5 ml.) and a slow stream of anhydrous HBr is bubbled through the solution for 90 minutes. The resin is filtered off and washed twice with 5 ml. of trifluoroacetic acid. The combined filtrates are concentrated in vacuo and excess HBr is removed from the peptide by repeated evaporations of methanol-water (1:1) solutions. The peptide is finally dissolved in water and lyophilised yielding aspartyl-propyl-ε-nitroarginine. The nitro group is then removed by hydrogenation in a Parr low pressure shaker hydrogenation apparatus as follows: The nitro protected tripeptide is dissolved in a mixture of methanol-acetic acid-water (10:1:1), about 10-20 mg./ml., and an equal weight of a 5% palladium on $BaSO_4$ catalyst is added and the mixture is shaken overnight at a hydrogen pressure of about 50 psi. The catalyst is removed by filtration and the filtrates are concentrated in vacuo. The peptide residue is chromatographed on a column of Sephadex G-25. The yield of the purified tripeptide as established by conventional amino acid analysis is approximately 24% based on the arginine incorporated in the resin. A portion of the product was hydrolysed with 5.7 N. HCl in water and assayed on an amino acid analyzer, which indicated a ratio of Asp 1.05, Pro 0.95, Arg 1.00.

Purity was determined by paper electrophoresis in the standard manner at a number of pH's.

EXAMPLE 2

Preparation of the Tetrapeptide Ser-Asp-Pro-Arg

The tripeptide resin from Example 1, not used in the synthesis of the tripeptide, was put through the deprotection cycle (see Example 1) and then was allowed to react with 0.111 g. of t-Boc-O-benzyl serine and 0.13 g. of dicyclohexylcarbodiimide in 20 ml. of methylene chloride as described in the synthesis cycle (Example 1).

A portion of the resin was then subjected to the cleavage and hydrogenation processes as described in Example 1 and recovered in the same manner as in Example 1 yielding Ser-Asp-Pro-Arg in a 20% yield based on arginine esterified to the resin. After hydrolysis with HCl, a sample of the recovered tetrapeptide was assayed on the amino acid analyzer, which indicated a ratio of Ser 0.79, Asp 1.18, Pro 1.02, and Arg 1.01. (Serine is partly destroyed during the acid hydrolysis.)

Purity was determined by paper electrophoresis in the standard manner at a number of pH's.

EXAMPLE 3

Preparation of the Pentapeptide Asp-Ser-Asp-Pro-Arg

A. The uncleaved tetrapeptide resin from Example 2 was subjected to the deprotection cycle (Example 1) and the synthesis cycle using 0.152 g. of t-Boc-$\beta$-benzylaspartate.

The resin portion had the pentapeptide cleaved therefrom with HBr in trifluoroacetic acid in the same manner as noted previously. The recovered polypeptide was dried in vacuo, thoroughly washed with water and then lyophilised. An analysis revealed a 16% yield based upon the arginine.

The pentapeptide product was hydrolyzed with HCl and assayed on an amino acid analyzer, which indicated a ratio of Asp 2.12, Ser 0.74, Pro 1.12, and Arg 1.01.

B. The pentapeptide is also prepared by a modification of the procedures of Examples 1–3A:

To a solution of 3.02 g. (6.82 mmoles) of $\alpha$-t-amyloxycarbonyl-$N^\epsilon$-tosyl-L-arginine (t-Aoc-tosyl-Arg) in 15 ml. of ethanol and 6 ml. of water is added dropwise a solution of caesium bicarbonate (1.4 g. in 3 ml. $H_2O$) until the pH of the solution is 7.0. The solution is concentrated in vacuo to a foam which is thoroughly dried in high vacuum over $P_2O_5$. To this residue is added 25 ml. of dry dimethylformamide (DMF) and 4.5 g. of chloromethylated resin (beaded copolystyrene-1% divinyl benzene containing 1.10 meg. of chloromethyl group/g. of resin) and the mixture is shaken at 50° C. for 3 days. The resin is filtered and washed with DMF (5×20 ml.), 90% DMF/$H_2O$ (3×20 ml.), DMF (2×20 ml.) and EtOH (2×20 ml.) and is then dried in vacuo over $P_2O_5$ giving 5.54 g. of argininated resin (ca. 50% incorporation).

This resin is then subjected to four cycles of deprotection and synthesis using 4 equivalents of the appropriate t-Boc-amino acid at each chain elongation step giving the protected pentapeptide resin material.

This resin material is then placed in an HF resistant reaction vessel, 8 ml. of anisole is added and the vessel is attached to an HF line. Approximately 70 ml. of HF is distilled into the reaction vessel at 0° C. and the mixture is stirred for a further 30 minutes at 0° C. The HF is pumped off and the resin is washed with ether (5×30 ml.) and then extracted with water (5×30 ml.). The aqueous layer is lyophilised to a yellow glassy powder which is purified according to Example 1 thereby giving the pentapeptide Asp-Ser-Asp-Pro-Arg.

The pentapeptide prepared above exhibits an $[\alpha]_D^{20°} = -78.6°$ (c=1, $H_2O$). Purity was determined by paper electrophoresis in the standard manner at a number of pH's.

EXAMPLE 4

Preparation of the Hexapeptide Ala-Asp-Ser-Asp-Pro-Arg

Another batch of arginated-resin (0.20 mmoles) was taken through the procedures of Examples 1–3A except that after the attachment of the second aspartic acid residue and deprotection an equivalent amount of t-BOC-alanine was coupled on with dicyclohexylcarbodiimide in the usual manner.

The resin was then subjected to the cleavage and hydrogenation processes as described in Example 1 and recovered in the same manner as in Example 1 yielding Ala-Asp-Ser-Asp-Pro-Arg in a 0.026 mmole, or 13%, yield.

The recovered polypeptide was assayed on an amino acid analyser, which indicated an amino acid ratio of Ala 0.95, Asp 2.05, Ser 0.08, Pro 0.98, and Arg 1.00.

Purity was determined by paper electrophoresis in the standard manner at a number of pH's.

EXAMPLE 5

Utilizing similar synthesis procedures to those described in Examples 1–4 above, the following polypeptides may be prepared:

Asp-Val-Asp-Leu-Ser
Thr-Ala-Ser-Thr-Glu
Asp-Val-Asp-Leu-Ser-Thr-Ala-Ser-Thr-Glu
Leu-Ser-Glu-Lys-His
Ala-Pro-Ser-Lys-Gly-Thr
Ala-Ser-Gly-Lys-Pro
Ala-Phe-Ala-Thr-Pro-Glu-Trp-Pro-Gly-Ser
Ala-Phe-Ala-Thr-Pro
Glu-Trp-Pro-Gly-Ser
Pro-Asp-Ala-Arg-His-Ser
Ala-Ser-Pro-Ser-Gln
Asp-Thr-Glu-Ala-Arg

EXAMPLE 6

Preparation of Metallic and Amine Salts

A. The pentapeptide Asp-Ser-Asp-Pro-Arg is converted to its sodium salt as follows:

A solution of the pentapeptide (0.05 mmoles) in water is carefully treated with exactly 1 equivalent of 0.1 N. NaOH and the monosodium salt of the peptide is isolated by lyophilisation. By the use of exactly 2 or 3 equivalents of 0.1 N. NaOH the corresponding di- and trisodium salts are obtained respectively.

Similarly, this peptide may be converted to other metallic salts, e.g., potassium, lithium, calcium, barium, magnesium, ammonium, ferrous, ferric, zinc, manganous, manganic, and aluminum salts, by substitution of the appropriate base.

B. The pentapeptide Asp-Ser-Asp-Pro-Arg is converted to its triethylamine salt as follows:

The careful addition of 1,2 or 3 equivalents of triethylamine to the solution of the peptide in methanol, followed by careful evaporation of the solvent, yields the mono-, bis- and tris-triethylammonium salts respectively. Similarly this pentapeptide may be converted to other amine salts, e.g., trimethylamine, tri(n-propyl) amine, dicyclohexylamine, β-(dimethylamino)ethanol, β-(diethyl-amino)ethanol, triethanolamine, tris(hydroxymethyl)amino-methane, arginine, lysine, histidine, N-ethylpiperidine, hydrabamine, choline, betaine, ethylenediamine, glucosamine, methylglucamine, theobromine, purine, piperazine, piperidine, caffeine and procaine salts, by substitution of the appropriate amine.

C. In a similar manner, the other peptides of Examples 1, 2, 4 and 5 may be converted to their corresponding metallic and amine salts.

EXAMPLE 7

The pentapeptide Asp-Ser-Asp-Pro-Arg is converted to its hydrochloride acid addition salt as follows:

Careful neutralization of a solution of the peptide in either water or methanol with exactly 1 or 2 equivalents of hydrochloric acid gives the mono- and dihydrochloride salts respectively. The salts are isolated either by lyophilisation of an aqueous solution or by precipitation with ether from a methanolic solution.

Similarly, this peptide may be converted to other acid addition salts, e.g., the hydrobromide, sulfate, phosphate, nitrate, acetate, oxalate, tartrate, succinate, maleate, fumarate, gluconate, citrate, malate, ascorbate, and benzoate salts, by substituting the appropriate acid for hydrogen chloride.

In a similar manner, the other peptides of Examples 1, 2, 4 and 5 may be converted to their corresponding acid addition salts.

EXAMPLE 8

Preparation of Esters

A. The appropriate peptide resin from Example 5 (1.0 g.) is suspended in anhydrous methanol (40 ml./g. of resin), triethylamine (50 mmoles) is added and the mixture is stirred at 22° C. for 20 hours. The resin is removed by filtration and the combined filtrates are concentrated in vacuo. The residue is dissolved in ethyl acetate, saturated with hydrogen chloride (5 ml.) and the solution is stirred at 22° C. for 30 minutes. The product is precipitated by the addition of ether giving a hydrochloride salt of the peptide. The O-benzyl ether protecting groups of Ser or Thr are removed by hydrogenolysis using Pd/BaSO$_4$ as described in Example 1 for the removal of the nitro group in nitroarginine derivatives, thereby giving Ala-Pro-Ser-Lys-Gly-Thr-OMe,
Ala-Ser-Gly-Lys-Pro-OMe,
Ala-Phe-Ala-Thr-Pro-OMe respectively.

By substituting other alcohols for methanol and raising the reaction temperature to 45°–80° C. and the reaction time to 45–90 hours there are obtained the corresponding ethyl, propyl, butyl, hexyl, octyl, decyl and dodecyl esters.

B. In this procedure a different type of anchoring bond is used for the attachment of the arginine residue, namely the resin —φ—CH$_2$—CH$_2$—C(CH$_3$)$_2$—OCONHNH$_2$ bond described by S. Wang and R. B. Merrifield in J. Amer. Chem. Soc. 91, 6488 (1969). Also, in this procedure N$^α$-2-(p-biphenylyl)isopropyloxycarbonyl (Bpoc) protecting groups are used instead of t-Boc for α-amino protection since the Bpoc group can be removed at each cycle of the synthesis with very mild acid under conditions where the anchoring bond is stable. The Bpoc-N$^ε$-nitro-Arg is attached to the resin by the DCC method and the synthesis is carried out essentially as described in Examples 1–3 except that 1% trifluoroacetic acid (TFA)/CH$_2$Cl$_2$ is used in the deprotection cycle in order to cleave the Bpoc group. The ultimate amino acid incorporated is protected as a N$^α$-benzyloxy-carbonyl derivative (Z) so that the N-terminus remains protected during the cleavage of the protected peptide from the resin. The cleavage is done as follows: 500 mg. of the peptide resin is supended in 12 ml. of 50% TFA in CH$_2$Cl$_2$ and the mixture is shaken at room temperature for 30 minutes. The resin is removed by filtration, washed with CH$_2$Cl$_2$ (2 × 10 ml.) and the combined filtrates are concentrated in vacuo giving Z-β-benzyl-Asp-O-benzyl-Ser-β-benzyl-Asp-Pro-N$^ε$-nitro-Arg-NHNH$_2$ as a white powder.

A solution of the protected peptide hydrazide (0.2 mmoles) in DMF (1 ml.) is cooled to −20° C. and 3.35 N. HCl in dioxane (0.5 mmoles) is added. The bath is warmed to −15° C. and t-butylnitrite (0.03 ml.) is added and the mixture is left at −10° C. for 10 minutes giving the peptide-azide derivative. An excess of methol is then added at −15° C. followed by ethyl diisopropylamine (0.5 mmoles) and the mixture is kept at 0° C. for 24 hours. During the first 6 hours, 5 μl. of the base are added every hour. The protected peptide is then precipitated by pouring the mixture into ice cold 1% acetic acid (15 ml.) and the precipitate is collected and washed by filtration. The benzyl based protecting groups are then removed by hydrogenolysis, as described in Example 1, and the product is purified by partition chromatography on Sephadex G-25 or by countercurrent distribution giving Asp-Ser-Asp-Pro-Arg-OMe.

By replacing methanol in this procedure by other alcohols there are obtained the corresponding ethyl, propyl, butyl, hexyl, octyl, decyl and dodecyl esters.

C. Utilizing similar procedures to those described in A and B, the corresponding esters of the polypeptides of Examples 1, 2, 4 and 5 may be prepared.

EXAMPLE 9

Preparation of Amides

A. The products of Example 8A and 8B are treated with a saturated solution of ammonia in methanol at room temperature for 2 days. The solvent is removed in vacuo to afford Ala-Pro-Ser-Lys-Gly-Thr-NH$_2$,
Ala-Ser-Gly-Lys-Pro-NH$_2$,
Ala-Phe-Ala-Thr-Pro-NH$_2$ and
Asp-Ser-Asp-Pro-Arg-NH$_2$, respectively.

B. The peptide-azide of Example 8B is reacted with ammonia in DMF solution under the conditions described in Example 8B for reaction with methanol. The protected peptide-amide is isolated and deprotected as described earlier giving Asp-Ser-Asp-Pro-Arg-NH$_2$.

C. The protected peptide resin product of Example 3A is suspended in a saturated solution of ammonia in methanol and the mixture is agitated at room temperature for 2 days. The resin is removed by filtration, washed with methanol and the combined filtrates are concentrated in vacuo giving t-Boc-Asn-O-benzyl-Ser- Asn-Pro-N$^\epsilon$-nitro-Arg-NH$_2$. The t-Boc group and the N$^\epsilon$-nitro group are then removed by acidic hydrolysis and hydrogenolysis respectively, as described above, giving Asn-Ser-Asn-Pro-Arg-NH$_2$.

By replacing ammonia with other amines, using DMF as solvent where appropriate and increasing the reaction temperature and time as necessary, there are obtained, for example, the corresponding dimethyl, diethyl, di(n-butyl), n-hexyl, piperidyl, pyrrolidinyl, morpholinyl, di(n-hexyl) and N-methylpiperazinyl amides.

D. Utilizing similar procedures to those described in A, B and C, the corresponding amides of the other polypeptides of Examples 1,2, 4 and 5 may be prepared.

EXAMPLE 10

Preparation of N-Acyl Derivatives

N$^\alpha$-Acyl derivatives of Asp-Ser-Asp-Pro-Arg are prepared by replacing the terminal t-Boc-amino acid (t-Boc-$\beta$-benzyl-aspartate) with the appropriate N$^\alpha$-acyl amino acid (e.g. N$^\alpha$-acetyl-$\beta$-benzylaspartate). All other steps in the deprotection, synthesis and cleavage cycles remain the same.

Thus, there may be prepared
N$^\alpha$-Acetyl-Asp-Ser-Asp-Pro-Arg
N$^\alpha$-Butryl-Asp-Ser-Asp-Pro-Arg
N$^\alpha$-Hexanoyl-Asp-Ser-Asp-Pro-Arg
N$^\alpha$-Octanoyl-Asp-Ser-Asp-Pro-Arg
N$^\alpha$-Decanoyl-Asp-Ser-Asp-Pro-Arg
N$^\alpha$-Dodecanoyl-Asp-Ser-Asp-Pro-Arg Similarly, the corresponding N$^\alpha$-acyl derivatives of other peptides mentioned in Examples 1,2,4 and 5 may be prepared.

EXAMPLE 11

Preparation of O-Acyl Derivatives

In order to prepare the protected pentapeptide resin material in which the hydroxyl group of serine is unprotected, the following modifcation of the solid phase synthesis is used.

The tripeptide resin material from Example 1 is subjected to the deprotection cycle and is then allowed to react with t-Boc-serine-N-hydroxysuccinimide ester giving t-Boc-Ser-$\beta$-benzyl-Asp-Pro-N$\epsilon$-nitro-Arg-resin which is then deprotected and coupled with p-nitrophenyl t-Boc-$\beta$-benzyl-aspartate under standard conditions, thereby giving t-Boc-$\beta$-benzyl-Asp-Ser-$\beta$-benzyl-Asp-Pro-N$\epsilon$-nitro-Arg-resin.

0.5 Mmoles of this protected peptide resin material is washed thoroughly with CHCl$_3$ and CH$_2$Cl$_2$ and 1.5 mmoles of hexanoic acid dissolved in 1:1 DMF/CHCl$_3$ is added followed by 1.5 mmoles of carbonyl diimidazole dissolved in the same solvents. The mixture is rocked in the Merrifield reaction vessel at room temperature for 2 hours and the peptide is then cleaved from the resin as described earlier. The N$^\epsilon$-nitro group is removed hydrogenolytically and the peptide is purified as described in earlier examples giving Asp-O-hexanoyl-Ser-As-Pro-Arg.

By replacing hexanoic acid with acetic acid, butyric acid, octanoic acid, decanoic acid and dodecanoic acid, the corresponding O-acetyl-butyryl, octanoyl, decanoyl and dodecanoyl compounds may be prepared.

Similarly, the corresponding O-acyl derivatives of the other peptides having side chain hydroxyl groups, mentioned in Examples 2,4 and 5, may be prepared.

EXAMPLE 12

The following illustrates typical pharmaceutical compositions of the compounds hereof, exemplified by Asp-Ser-Asp-Pro-Arg:

| Aerosol Formulation (per dose) | |
|---|---|
| Asp-Ser-Asp-Pro-Arg | 10 mg. |
| Sodium chloride | 6.9 mg. |
| Sodium monobasic phosphate monohydrate | 5.8 mg. |
| Water to make | 1.0 ml. |
| Injectable Formulation (per dose) | |
| Asp-Ser-Asp-Pro-Arg | 10 mg. |
| Sodium chloride | 6.9 mg. |
| Sodium monobasic phosphate monohydrate | 5.8 mg. |
| Methylparaben | 0.25 mg. |
| Propylparaben | 0.14 mg. |
| Water to make | 1.0 ml. |
| Dry Powder Formulation for Inhalation with device such as Spinhaler$^R$ (per dose) | |
| Asp-Ser-Asp-Pro-Arg | 10 mg. |
| Lactose | 30 mg. |

EXAMPLE 13

The "blocking" activity of the polypeptides of the invention can be assayed by utilization of the classic Prausnitz-Kustner (P-K) reaction. In this classic method, a known allergic serum i.e., one that contains IgE specific for a known antigen or allergen is injected intradermally into a human volunteer. After waiting a period of time, e.g. 20 or more hours, the injected sites are then challenged with a prick or injection of a solution of an antigen that is specific for the IgE in the injected serum. Within the next 10 to 30 minutes a positive reaction is evidenced by the development of a wheal (and flare) at the injected site. The more extensive the diameter of the wheal the more intensive is the allergic reaction. That is, a more extensive wheal indicates a greater release of histamine into the tissues at the injected site. Conversely, the development of wheals of lesser diameter or the absence of any wheal at all indicates diminished allergic reaction and/or no allergic reaction at all. The P-K reaction as noted above is a classic test and is universally known and utilized by allergists.

As noted above, the classic P-K reaction is utilized to assay the "blocking" abilities of the polypeptides utilized in the present invention.

The following describes assays of a number of polypeptides useful in the present invention, the synthesis of which was described hereinabove.

All of these assays were performed using a single proven safe P-K donor serum that contains IgE specific for guinea pig allergens.

Peptide solutions were either injected intradermally 1 to 24 hours prior to the P-K serum, or mixed with dilutions of the P-K serum for simultaneous injection. Initial tests were performed using the P-K serum at from 1:4 to 1:200 dilutions. Further studies were run at a fixed P-K dilution of 1:32 while the invention peptide solutions were varied to contain from about 1 mM to 2 M of the peptide being tested. Injected sites on the volunteers were challenged by prick-puncture of guinea pig BCA 1:40 w/v (purchased from Berkeley Biologicals, Inc.).

Human volunteers were chosen who had serum IgE levels below 100 U/ml. (242 ng/ml.) which levels have been previously shown to assure successful P-K reactivity. In addition, for the purpose of these tests, the individuals were chosen who had a negative direct skin test to guinea pig antigen. P-K and skin tests were performed on the back and/or forearm. Multiple test sites of approximately 25 mm diameter were circled with a marking pen and all injections were made within the circled skin areas.

A typical sequence of events was intradermal injection of 0.1 ml. of the peptide solution or control buffered saline diluent solution; followed in 1 to 24 hours by intradermal injection of 0.05 ml. of P-K serum into each of the previously injected sites. After 20 to 24 hours had elapsed, each site was prick-punctured with the antigen solution, blotted dry in 5 minutes and measurements of the wheal and flare in both their narrowest and widest diameter were made three tiems, usually 15, 20 and 25 minutes after prick-punctures.

Blocking activity assays were undertaken with the following polypeptides: Asp-Pro-Arg; Ser-Asp-Pro-Arg; Asp-Ser-Asp-Pro-Arg; and Ala-Asp-Ser-Asp-Pro-Arg. For comparison testing, Asp-Thr-Glu-Ala-Arg and tosyl-L-arginine sarcosine methylester (TASME), were also synthesized and tested.

The above-noted polypeptides were assayed as noted above on six different individuals. Results were as follows:

For Asp-Pro-Arg, the average % inhibition was 15% with an individual range from as low as 0% to as high as 38%.

For Ser-Asp-Pro-Arg, the average inhibition was 18%, with an individual low of 0% and a high of 50%.

For Asp-Ser-Asp-Pro-Arg, the average inhibition was 72%, with an individual low of 60%, and a high of 89%.

For Asp-Thr-Glu-Ala-Arg, the average inhibition was 58%, with an individual low of 30%, and a high of 80%.

For TASME, the average inhibition was 24%, with a low of 0% and a high of 40%.

The results, as noted above, present the average of measurements at three time intervals, in duplicate, for each reaction in each individual, subtracted from the average control wheal measurements, and divided by the average measurement of each individual's control wheal. Control wheals in different individuals varied from 8 to 40 mm$^2$ with a mean of 17 mm$^2$. Each peptide was utilized at approximately 6 μg/ml. dilution and 0.1 ml. was injected at each site, followed by 0.05 ml. of diluted P-K serum containing 0.2 ng. of IgE. Thus, $10^{-9}$M of the peptide was competing with $10^{-15}$M of the IgE for the binding sites on mast cells, or a ratio of one IgE molecule to $10^6$ peptide molecules. From the above assays, it appears that the pentapeptide, i.e., Asp-Ser-Asp-Pro-Arg, exhibits the strongest "blocking" activity, with the hexapeptide, i.e., Ala-Asp-Ser-Asp-Pro-Arg, exhibiting somewhat less activity. The tetrapeptide, Ser-Asp-Pro-Arg and the tripeptide Asp-Pro-Arg, exhibited the least activity.

It should be noted that the pentapeptide Asp-Thr-Glu-Ala-Arg was prepared and assayed along with the other peptides as described above. This particular polypeptide does not have an analogous sequence of amino acids appearing in the $C_\epsilon 2$, $C_\epsilon 3$ or $C_\epsilon 4$ domains of the IgE molecule, yet it exhibits a high activity in the assay test.

EXAMPLE 14

It has also been determined that the active polypeptides of the invention appear to have the ability to "displace" IgE from mast cells as well as to prevent the binding of the IgE to the receptors. In a single test, an individual known to have extreme sensitivity to guinea pig antigens, that is a person with a high natural concentration of guinea-pig-antigen-sensitive IgE, was injected with polypeptides in accordance with the invention, and his reaction to guinea pig antigen was noted.

Specifically, approximately 2 nM each of Asp-Ser-Asp-Pro-Arg and Ala-Asp-Ser-Asp-Pro-Arg were each intradermally injected into 3 marked sites. For comparison, TASME, as well as a control of the buffer diluent alone, was also each injected into 3 marked sites. At one, five and twenty-four hours subsequent to the polypeptide and control injection, one of each peptide and one diluent site were prick-puncture challenged with guinea pig antigen. No inhibition of the wheal and flare reaction was observed at any site at the one and five hour intervals. However, at the twenty-four hour challenge, the wheal at the Asp-Ser-Asp-Pro-Arg site was approximately 45% smaller; while at the Ala-Asp-Ser-Asp-Pro-Arg site, the wheal was approximately 23% smaller. No reduction in the size of the wheal was observed at the TASME site compared to the buffered saline diluent site.

It thus appears that, at least that most active of the peptides of the invention, will "displace" IgE already bound to mast cell sites, thus inhibiting a natural allergic reaction. As has previously been demonstrated in Example 13 this same pentapeptide is extremely effective in inhibiting a passively transferred (P-K) allergic reaction.

EXAMPLE 15

Acute toxicity was determined as follows:

DBA white mice (average weight 15 g.) were each injected with 1.4 ml. of a solution of the peptide in phosphate buffered saline, pH 7.4, as follows:

| | |
|---|---|
| 0.1 ml. × 3 | intradermally |
| 0.1 ml. × 3 | subcutaneously |
| 0.2 ml. | intravenously |
| 0.6 ml. | intraperitoneally |

24 to 72 hours post-injection the mice (all still living) were killed and autopsied.

The peptides and concentrations used were as follows:

Ala-Asp-Ser-Asp-Pro-Arg (Example 4) 5 μg/ml. (375 mg/kg)—6 mice

Asp-Ser-Asp-Pro-Arg (Example 3) 10 μg/ml. (1 mg/kg)—8 mice

Asp-Ser-Asp-Pro-Arg (Example 3) 13 μg/ml. (1.3 mg/kg)—8 mice

Post-mortem gross and microscopic examination of tissues and organs indicated no local or systemic toxicological abnormalities.

The N-acyl derivatives also appear to be active in inhibiting IgE binding to mast cells and leucocytes. This "blocking" activity appears to be related, at least in part, to the lipophilic strength of the acyl moiety. The peptides themselves are hydrophilic, and it is postulated that mast cells and leucocytes binding may be enhanced by providing the peptide with a strongly lipohilic substituent, since the cell material itself, is, in considerable part, lipids. Thus, N-acyl derivatives of the peptides of the invention having relatively long carbon chain substitents, say 8 or more carbon atoms, would have enhanced lipophilic properties and concurrent "blocking" activity.

EXAMPLE 16

In this regard, the 8 carbon chain acyl substituted peptide, octanoyl-Asp-Ser-Asp-Pro-Arg, as well as the 3 carbon chain acyl substituted peptide, acetoyl-Asp-Ser-Asp-Pro-Arg, were prepared by the method outlined in Example 10 above. These peptides were tested, in vitro, for their blocking ability with respect to the Wil-2WT human lymphoblastoid tissue culture cell line as follows.

Wil-2WT cells in culture medium were centrifuged at about 2000 RPM. The separated cells were mixed with minimal essential medium (MEM) and recentrifuged at 2000 RPM. The supernatent was decanted off completely and the residual cells were suspended in MEM+3% human serum albumin (HSA). The cell suspension was divided into suitable aliquots in reaction tubes. Blanks and control reaction tubes were also prepared. To various of the cell suspension tubes, were added known amount of Sha Myeloma E; Sha Myeloma E and octanoyl-Asp-Ser-Asp-Pro-Arg; or Sha Myeloma E and acetoyl-Asp-Ser-Asp-Pro-Arg. After mixing and standing at room temperature for approximately one hour, a known quantity of deaggregated IgE, tagged with radioactive iodine ($I^{125}$) was added to the tubes. After standing a short time, the capped tubes were mixed by slow inversion over an hour's time. All the reaction tubes were then centrifuged and the supernatent was decanted, leaving the cell pellets behind. The pellets were washed four times with phosphate buffered saline; and then finally resuspended in phosphate buffered saline. The suspension was then counted on a gamma counter in order to determine the amount of tagged IgE bound to the Wil-2WT cells.

In several such procedures, it was determined that octanoyl-Asp-Ser-Asp-Pro-Arg yielded as high as a 25% blocking of the binding of IgE to the lymphoblastoid culture cells. On the other hand, the acetoyl derivative did not exhibit any blocking ability whatsoever.

The substitution of a lipophilic N-acyl moiety onto the polypeptides of the invention therefore appears to provide a useful addition to the non-substituted polypeptides noted hereinabove.

Utilizing in vitro procedures as noted in Example 16 above, a number of polypeptides of the invention having amino acid sequences of high interest, were reviewed for their ability to block IgE from Wil-2WT cells. The hexapeptide corresponding to the 476-481 amino acid sequence in IgE's Fc region, i.e., Pro-Asp-Ala-Arg-His-Ser, in such testing, has exhibited as high as a 28% block. Based on such in vitro testing it appears that the polypeptides in this region of the Fc chain could possibly have blocking activities approaching that of the Asp-Ser-Asp-Pro-Arg pentapeptide and its related hexa-, tetra-, and tri-peptides.

Certain of the amino acids appearing in protein contain within their molecular structure, the sulf-hydryl (—S—H) linkage. Such amino acids, i.e., cysteine, are capable of forming a di-sulfide bridge with a corresponding amino acid to form the dimer, i.e., cystine. That is, the occurance of cysteine, $HSCH_2.CH(NH_2)$—COOH, as well as its dimer, cystine, $[—SCH_2.CH(NH_2).COOH]_2$ has been shown. It is also possible to condense two cysteine molecules with their single sulf-hydryl groupings into cystine with its cross-linking disulfide —S—S— bond.

It is also possible, utilizing well known techniques, to cross-link peptides through such —S—S— bonding where cysteine occurs in the peptide chains.

In the present instance, at least one dimer peptide and several derivatives, have been prepared and tested for possible IgE blocking activity. Thus, the most active pentapeptide Asp-Ser-Asp-Pro-Arg has been cross-linked to form the dimer peptide through the nearest cysteine occurring in the Fc chain. Specifically, a cysteine occurs at the 318 position, just 2 amino acids away from the first aspartic acid (320) occurring in the preferred pentapeptide. Thus, the equivalent dimer, i.e., [-Cys-Ala-Asp-Ser-Asp-Pro-Arg]$_2$ has been prepared and tested against radioisotope labelled IgE and the Wil-2WT tissue culture as noted previously in example 16, above.

In two such experiments the dimer [-Cys-Ala-Asp-Ser-Asp-Pro-Arg]$_2$ yielded blocking effects of 6% and 5% respectively.

A number of analogues of the preferred pentapeptide Asp-Ser-Asp-Pro-Arg, and of its dimer [-Cys-Ala-Asp-Ser-Asp-Pro-Arg]$_2$ were prepared and tested by the same technique as described in Example 16, above. Specifically, asparagine was substituted for aspartic acid in the above noted peptides in various configurations, i.e., (a) Asp-Ser-Asn-Pro-Arg
(b) Asn-Ser-Asp-Pro-Arg
(c) Asn-Ser-Asn-Pro-Arg
(d) [-Cys-Ala-Asp-Ser-Asn-Pro-Arg]$_2$
(e) [-Cys-Ala-Asn-Ser-Asp-Pro-Arg]$_2$
(f) [-Cys-Ala-Asn-Ser-Asn-Pro-Arg]$_2$ The noted analogues were prepared in accordance with well-known peptide synthesis techniques such as noted, for instance, in Examples 1,2,3, etc. above. The mono-peptides were also cross-linked through the cysteine moiety to form the noted dimers.

These analogues were then tested for their "blocking" activities in accordance with the procedure of Example 16.

Analogue (a) exhibited activities of 5% and 6% in two trials; analogue (b), less activity at 5% and 3%; while analogues (c) was even less active at 4% and 2%. On the other hand, dimer (d) exhibited very low, if any, activity at 0 and 2%, but dimer (f) exhibited activity of 9% and 12%. Dimer (d) was, however, not tested in these series of trials.

While none of the Asn analogues exhibited activities comparable with these preferred peptides, there is indication, that some such variations may be useful in practicing the invention method of blocking the human allergic response.

What is claimed is:

1. A method for blocking the mammalian allergic reaction which method comprises administering to a host subject in an effective amount of a polypeptide comprising from 3-10 amino acids in sequence, said sequence selected from a portion of the amino acid sequence 265-537 of the Fc region of Immunoglobulin E, or the polypeptide Asp-Thr-Glu-Ala-Arg, or a pharmacologically acceptable salt or derivative thereof.

2. The method of claim 1 wherein the polypeptide is Asp-Ser-Asp-Pro-Arg.

3. The method of claim 1 wherein the polypeptide is Ala-Asp-Ser-Asp-Pro-Arg.

4. The method of claim 1 wherein the polypeptide is Ser-Asp-Pro-Arg.

5. The method of claim 1 wherein the polypeptide is Ala-Ser-Gly-Lys-Pro.

6. The method of claim 1 wherein the polypeptide is Leu-Ser-Gln-Lys-His.

7. The method of claim 1 wherein the polypeptide is Thr-Ala-Ser-Thr-Glu.

8. The method of claim 1 wherein the polypeptide is Asp-Val-Asp-Leu-Ser.

9. The method of claim 1 wherein the polypeptide is Asp-Pro-Arg.

10. The method of claim 1 wherein the polypeptide is Ala-Pro-Ser-Lys-Gly-Thr.

11. The method of claim 1 wherein the polypeptide is Ala-Phe-Ala-Thr-Pro.

12. The method of claim 1 wherein the polypeptide is Glu-Trp-Pro-Gly-Ser.

13. The method of claim 1 wherein the polypeptide is Pro-Asp-Ala-Arg-His-Ser.

14. The method of claim 1 wherein the polypeptide is Ala-Ser-Pro-Ser-Gln.

15. The method of claim 1 wherein the polypeptide is Asp-Val-Asp-Leu-Ser-Thr-Ala-Ser-Thr-Gln.

16. The method of claim 1 wherein the polypeptide is Ala-Phe-Ala-Thr-Pro-Glu-Trp-Pro-Gly-Ser.

17. The method of claim 1 wherein the polypeptide is Asp-Thr-Glu-Ala-Arg.

* * * * *